US00PP25042P3

(12) United States Plant Patent
Austin

(10) Patent No.: US PP25,042 P3
(45) Date of Patent: Nov. 11, 2014

(54) SHRUB ROSE PLANT NAMED 'AUSWASHER'

(50) Latin Name: *Rosa hybrida*
Varietal Denomination: AUSwasher

(71) Applicant: David Austin Roses Ltd., Wolverhampton (GB)

(72) Inventor: David J. C. Austin, Wolverhampton (GB)

(73) Assignee: David Austin Roses Ltd., Albrighton, Wolverhampton (GB)

( * ) Notice: Subject to any disclaimer, the term of this patent is extended or adjusted under 35 U.S.C. 154(b) by 0 days.

(21) Appl. No.: 13/694,537

(22) Filed: Dec. 11, 2012

(65) Prior Publication Data

US 2014/0165238 P1 Jun. 12, 2014

(51) Int. Cl.
*A01H 5/00* (2006.01)

(52) U.S. Cl.
USPC ..... Plt./106

(58) Field of Classification Search
USPC ..... Plt./107, 106, 136, 137, 138
See application file for complete search history.

*Primary Examiner* — Wendy C Haas
(74) *Attorney, Agent, or Firm* — KPPB LLP

(57) ABSTRACT

A variety of rose plant of the shrub class, named 'AUSwasher'. The 'AUSwasher' is a variety of cut-rose rose with an unusual characteristic of large, green pistils protruding from the center of the quartered blossoms, with a strong fragrance and long vase life.

1 Drawing Sheet

Classification: The present invention relates to a new *Rosa hybrida* shrub of the market class 'English Rose'.

Variety denomination: The new plant has the varietal denomination 'AUSwasher.'

ORIGIN OF INVENTION

This invention relates to a new and distinct variety of shrub rose plant named 'AUSwasher', which was originated from the cross-pollination of the two 'unnamed' seedlings of *Rosa hybrida.*

BACKGROUND OF THE INVENTION

The primary objective of this breeding was to produce a variety of cut-rose rose with an unusual characteristic of large, green pistils protruding from the center of the quartered blossoms, with a strong fragrance and long vase life.

SUMMARY OF THE INVENTION

Among the features which distinguish the new variety from others presently available and commercial rose cultivars known to the inventor is the following combination of characteristics: green pistils protruding from the center of the bloom, quartered blooms, a strong old rose fragrance that develops into myrrh as the flower ages, and long vase life.

Asexual reproduction of the new variety by budding as performed in greenhouses at Bowling Green Lane in Albrighton, Britain shows that the foregoing and other distinguishing characteristics come true to form and are established and transmitted through succeeding asexual propagations. 'AUSwasher' may be asexually propagated by budding. The budding successfully occurred on the plant/rootstock *Rosa* 'Natal Briar' (not patented) for the observed plants.

COMPARISON WITH PARENTS

The seed and pollen parents of 'AUSwasher' are two unnamed seedlings. The new rose may be distinguished from its seed parent, by the following combination of characteristics: the parent has blooms that are deeply-cupped pink which are smaller in size and the pistil do not protrude from the center of the bloom. The new rose may be distinguished from its pollen parent, by the following combination of characteristics: the parent has blooms that are pale apricot cupped flowers, again with no pistils protruding from the center of the bloom.

COMPARISON WITH THE CLOSEST COMMERCIALLY AVAILABLE CULTIVAR

The closest commercially available cultivars to the new variety are the 'AUSimmon' (U.S. Plant Pat. No. 17,267). The new rose may be distinguished from the 'AUSimmon' variety by the following combination of characteristics: the 'AUSwasher' has pistils that protrude from the center of the bloom, whereas 'AUSimmon' does not, and also bears double blooms of a slightly deeper pink and green outer petals. 'AUSimmon' although a double bloom has fewer petals than 'AUSwasher'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSwasher' specimens were made at the nursery at David Austin Roses Limited in Albrighton, Wolverhampton, United Kingdom. The following description is of 1 year-old rose plants of the new variety grown in a greenhouse environment in Albrighton, Britain in the month of September. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 2.5 cm long and 2 cm in diameter when the petals start to unfurl.

*Form*.—The bud form is globular.

*Color*.—When sepals first divide, the bud color is RHS 36D (red group). When half blown, the upper sides of the petals are RHS 36D (red group).

*Calyx*.—Shape: star-shaped when fully opened with the sepals folding back. Length: 10 cm. Diameter: 10 cm.

*Sepals*.—Arrangement: Regular. Color: Upper Surface: green RHS 194A (greyed-green group). Lower Surface: green RHS 138B (green group). Length: 5 cm. Width: 6-9 mm. Shape: Lanceolate. Surface texture: Upper Surface: Downy. Lower Surface: Smooth. Number: There are 3 normally appendaged sepals, and 2 unappendaged sepals with glandular edges.

*Receptacles*.—Color: RHS 138B (green group). Shape: funnel. Size: slender, about 1 cm long×8 mm wide. Surface: Smooth.

*Peduncle*.—Length: medium, averaging about 8 cm. Surface: Glandular. Color: RHS 138B (green) with some RHS 178B (greyed-red group). Strength: Strong.

Blooms:

*Size*.—Large, average open diameter is about 11 cm.

*Borne*.—Singly.

*Stems*.—Strength: Strong, average length is about 65 cm. Diameter: 6 mm.

*Form*.—When first open, bloom is cupped. Permanence of bloom: outer petals curl back.

Petalage: Number of petals under normal conditions: 153.

*Color*.—The upper sides of the petals are RHS 49C-D (red group). The reverse sides of the petals are RHS 49D (red group), and the base of the petals has RHS 11D (yellow group).

*Variegations*.—None.

*Discoloration*.—The general tonality at the end of the first day is white RHS 49C-D (red group), and at the end of the third day is RHS 49C-D (red group).

*Fragrance*.—Strong. Character of fragrance: old rose, developing myrrh later.

Petals:

*Texture*.—Velvety.

*Size*.—Width: 3 cm. Length: 4.5 cm.

*Surface*.—Smooth.

*Shape*.—Deltoid.

*Margin*.—Mostly entire, some notched.

*Apex shape*.—Rounded.

*Base shape*.—Pointed.

*Form*.—Mostly incurved — some inner petals folded with outer petals almost flat.

*Arrangement*.—Quartered.

*Petaloids*.—Number: None.

*Persistence*.—Petals drop off cleanly before drying.

*Lastingness*.—On the plant: About 9 days. As a cut flower: About 8 days.

Reproductive parts:

*Stamens*.—Number: 70. Length: 9 mm.

*Anthers*.—Length: 2-5 mm. Color: RHS 15A (yellow-orange group). Arrangement: regular around styles.

*Filaments*.—Color: RHS 13C (yellow group). Length: 3-7 mm.

*Pollen*.—Color: RHS 15A (yellow-orange group).

*Pistils*.—Number: 10. Length: 15 mm.

*Styles*.—Color: RHS 157D (green-white group). Length: 14 mm.

*Stigmas*.—Color: RHS 178B (greyed-red group). Length: 1 mm.

*Hips*.—None Observed.

PLANT CHARACTERISTICS

Plant form: Bush.

Plant growth: Vigorous.

Age to maturity: One year.

Mature plant: Height: 110 cm. Width: 90 cm.

Rootstock: *Rosa* 'Natal Briar' for the observed plants.

Foliage:

*Number*.—Leaflets on normal mid-stem leaves is: 5.

*Size*.—Medium, about 15 cm long×12 cm wide.

*Quantity*.—Normal. Number of leaves per flowering stem is: 18.

*Color*.—New foliage: Upper side: yellow/green RHS 138A (green group) with some RHS 178B (greyed-red group). Lower side: yellow/green RHS 138B (green group). Old foliage: Upper side: RHS 139B (green group). Lower side: RHS 138A (green group).

Leaflets:

*Size*.—About 7 cm long×5 cm wide.

*Shape*.—Broadly oval.

*Base shape*.—Rounded.

*Apex shape*.—Acuminate.

*Texture*.—Leathery.

*Edge*.—Serrated.

*Serrations*.—Single and large.

*Petiole*.—Color: RHS 38B (green group) with topside overlaid with RHS 178B (greyed-red group). Length: 3.5 cm. Width: 2 mm. Surface Texture: Smooth.

*Petiole rachis*.—Color: RHS 38B (green group) with topside overlaid with RHS 178B (greyed-red group). Underside: with prickles.

*Stipules*.—Length: 1.8 cm, smooth. Color: RHS 138B (green group).

*Auricle*.—Shape: Lanceolate. Length: 6 mm. Width: 1.5 mm. Color: RHS 138B (green group).

*Vein color*.—Same as leaf color.

*Venation pattern*.—Reticulate.

Wood:

*New wood*.—Color: RHS 178B (greyed red). Bark: Smooth.

*Old wood*.—Color: RHS 139A (green group). Bark: Smooth.

Branching habit:

*Number*.—The main stems are cut to allow stem to shoot with no branching. Observation did not ascertain a natural branching habit.

Stems:

*Mature stem*.—Length: 70 cm. Diameter: 6 mm.

*Internode distance*.—7 cm. The above measurements are all variable, depending on growing conditions in a season.

*Stem pubescence present*.—No.

Prickles:

*Quantity*.—On main canes from base: Ordinary. Number per stem length: 15 per 10 cm.

*Form*.—Deep concave.

*Length*.—6 mm.

*Color when young*.—RHS 183A (greyed-purple group).

*Color when mature*.—RHS 183A (greyed-purple group).

Small prickles:

*Quantity*—Main stalk: None. Number per stem length: N/A. Laterals: None. Number per stem length: N/A.

Disease resistance:

*Mildew*.—Resistant.

*Blackspot*.—Resistant.

*Rust*.—Resistant.

Pest resistance: Not tested.

Winter hardiness: Not tested.

Growing conditions: Normal greenhouse growth conditions.

What is claimed is:

1. A new and distinct variety of rose plant of the shrub class suitable for cut flower production, substantially as herein shown and described.

* * * * *

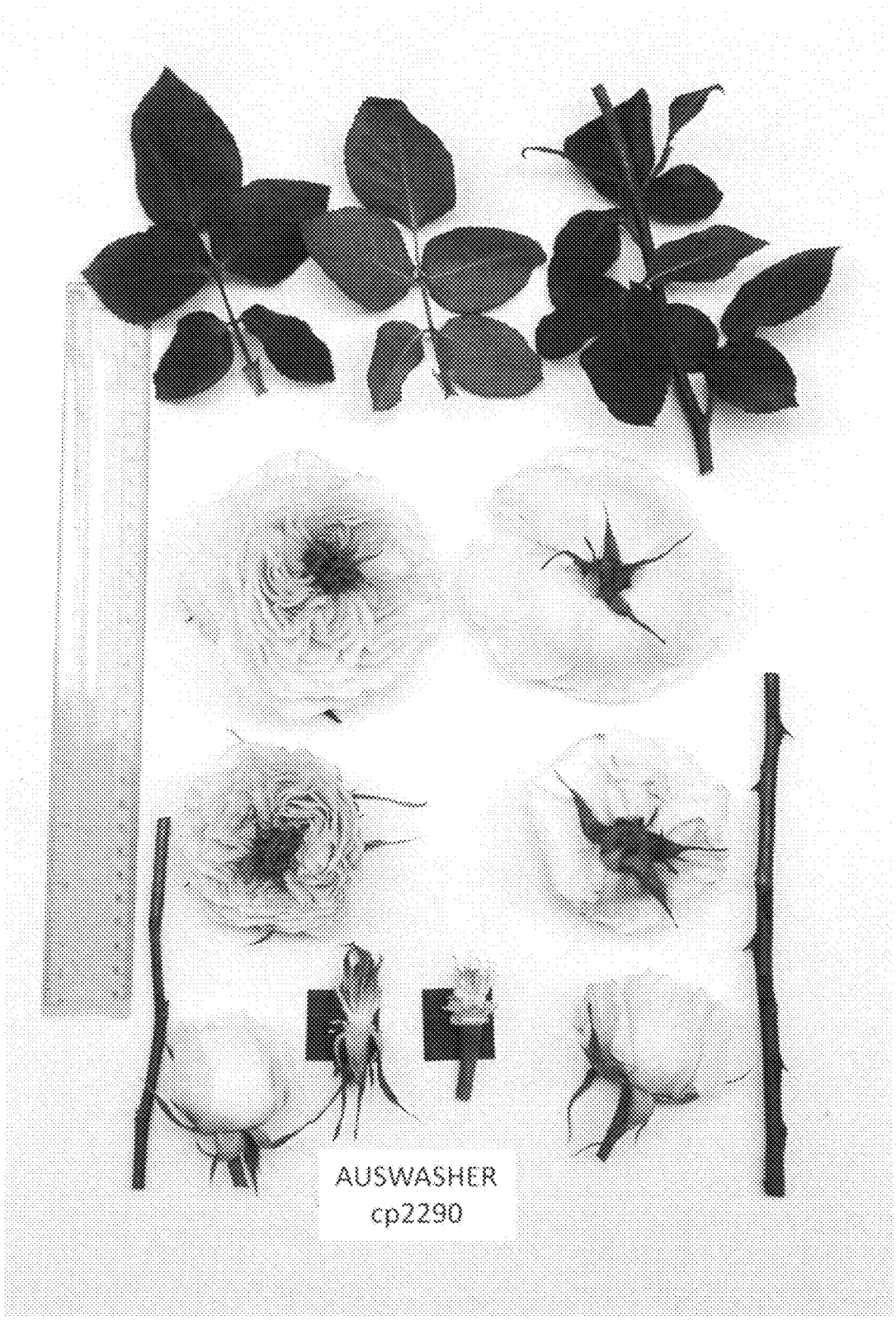
AUSWASHER
cp2290